US006417201B1

(12) United States Patent
Bardsley et al.

(10) Patent No.: US 6,417,201 B1
(45) Date of Patent: *Jul. 9, 2002

(54) LEVOBUPIVACAINE AS AN ANALGESIC AGENT

(75) Inventors: Hazel Judith Bardsley; Robert William Gristwood; Andrew John McGlashan Richards, all of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/614,615

(22) Filed: Jul. 12, 2000

Related U.S. Application Data

(63) Continuation of application No. 09/210,966, filed on Dec. 14, 1998, now Pat. No. 6,103,741, which is a continuation of application No. 08/549,408, filed on Oct. 27, 1995, now Pat. No. 5,849,763, which is a continuation-in-part of application No. PCT/GB94/02249, filed on Oct. 13, 1994.

(30) Foreign Application Priority Data

Oct. 13, 1993 (GB) ............................................... 9321061
Apr. 22, 1994 (GB) ............................................... 9408014
Apr. 13, 1995 (GB) ............................................... 9507677

(51) Int. Cl.⁷ .......................................... A61K 31/445

(52) U.S. Cl. ..................................................... 514/330

(58) Field of Search ......................................... 514/330

(56) References Cited

U.S. PATENT DOCUMENTS 4,695,576 A    9/1987   af Ekenstam et al . ...... 514/330

FOREIGN PATENT DOCUMENTS

WO    9632109    10/1996

OTHER PUBLICATIONS

Gristwood et al., Exp. Opin. Invest. Drugs, 3(11), 1209–1212 (1994).*
Testa, B. et al. (1990) "Racemates Versus Enantiomers in Drug Development: Dogmatism or Pragmatism?" Chirality, vol. 2, pp. 129–133.
Rutten, A. J. et al. (1993) "Tissue distribution of bupivacaine enantiomers in sheep" Chirality, vol. 5, No. 7, pp. 485–491.
Abreg, G. (1972) "Toxicological and local anaesthetic effects of optically active isomers of two local anaesthetic compounds" Acta Pharmacologia Et Toxicologica, vol. 31, pp. 273–286.
Kuhnert, B. R. et al. (1981) "Bupivacaine disposition in mother, fetus and neonate" Federation Proceedings, vol. 40, No. 31, p. 684.
Ariens, E. J. (1991) "Racemic therapeutics—ethical and regulatory aspects" Eur. J. Clin. Pharmacol., vol. 41, No. 2, pp. 89–93.

Rutten, A. J. et al. (1991) "Cardiovascular Effects and Regional Clearances of I.V. Bupivacaine in Sheep: Enantiomeric Analysis" Br. J. Anaesth., vol. 67, No. 3, Sep., pp. 247–256.
Luduena, F. P. et al. (1972) "Optical Isomers of Mepivacaine and Bupivacaine" Arch. Int. Pharmacodyn. Ther., vol. 200, No. 2, Dec., pp. 359–369. (1972).
Rutten, A. J. et al. (1992) "7Postoperative course of plasma protein binding of lignocaine, ropivacaine and bupivacaine in sheep" J. Pharm. Pharmacol., vol. 44, No. 4, Apr., pp. 355–358.
Lee–Son, S. et al. (1992) "Stereoselective Inhibition of Neuronal Sodium Channels by Local Anaesthetics" Anesthesiology, vol. 77, No. 2, Aug., pp. 324–335.
Wang, G. K. et al. (1992) "Altered Stereoselectivity of Cocaine and Bupivacaine Isomers in Normal and Batrachotoxin–modified Na+ Channels" J. Gen. Physiol., vol. 100, No. 6, Dec., pp. 1003–1020.
Clark, B. J. et al. (1991) "Reversed–phase and chiral high–performance liquid chromatographic assay of bupivacaine and its enantiomers in clinical samples afer continuous extrapleural infusion" J. Chromatog., vol. 553, pp. 383–390.
Ariens, E. J. (1990) "Racemische therapeutica probleemmiddelen" Pharmaceutisch Weedblad, vol. 125, No. 2, Jun., pp. 552–554.
Ariens, E. J. (1990) "Stereoselectivity in pharmacodynamics and pharmacokinetics" Schweiz. Med. Wochenschr., vol. 120, No. 5, Feb., pp. 131–134.
Rowland, Malcolm and Thomas N. Tozer (eds) In: Clinical Pharacokinetics Concepts and Applications, Chapter 7, pp. 83–88, (1995) Williams and Wilkins publishers.
Mather, L.E. (1991) "Disposition of Medivacaine and Bupivacaine Enantiomers In Sheep" British Journal of Anaesthesia 67:239–246.
Du Pen, Stuart L. et al. (1992) "Chronic epidural bupivacaine–opioid infusion in tractable cancer pain" Pain 49:293–300.
Honerjager, P. (1986) "The contribution of Na channel block to the negative inotropic effect of antiarrhythmic drugs" Basic Res. Cardiol. 81 (Suppl 1):33–37.
Fozzard, Harry A. and J. Andrew Wasserstrom (1985) "Voltage Dependence of Intracellular Sodium and Control of Contraction" In Zipes DP, Jalife E (eds) Grune & Stratton, Orlando, pp. 51–57.

(List continued on next page.)

Primary Examiner—Phyllis G. Spivack
(74) Attorney, Agent, or Firm—Saliwanchik, Lloyd & Saliwanchik

(57) ABSTRACT

Levobupivacaine ((S)-1-butyl-N-(2,6-dimethylphenyl)-2-piperidinecarboxamide) is useful as an anesthetic, particularly in a patient who is disposed to adverse systemic side-effects, e.g., one who is CNS-compromised or predisposed to CNS side-effects. A unit dose of levobupivacaine comprising at least 75 mg to less than 200 mg of levobupivacaine is described herein.

1 Claim, No Drawings

OTHER PUBLICATIONS

Schlepper, M. (1989) "Cardiodepressive effects of antiarrhythmic drugs" European Heart Journal 10(Suppl. E):73–80/

Reiz, S. and S. Nath, (1986) "Cardiotoxicity Of Local Anaesthetic Agents" Er. J. Anaesth. 58:736–746.

De Jong, Rudolph H., Nancy L. David (1981) "Treating Bupivacaine Arrhythmais: Preliminary Report" Reg Anesth 6:99–103.

Strichartz, Gary R. (1988) "Neural physiology and local anesthetic action" In: Neural Blockade In Clinical Anesthesia And Management Of Pain, Cousins MJ, Bridenbaugh PO (eds), J B Lippincott Company, Philadelphia, pp. 25–45.

Butterworth, J.F. et al. (1993) "Bupivacaine Inhibits Cyclic–3', 5'–Adenosine Monophosphate Production" Anesthesiology 79:88–95.

Mazoit, J.X. et al. (1993) "Myocardial Uptake of Bupivacaine: II. Pharmakinetics and Pharmacodynamics of Bupivacaine Enantiomers in the Isolated Perfuse Rabbit Heart" Anesth. Analg. 77(3):477–482.

Clarkson, C.W., L.M. Hondeghem (1985) "Mechanism for Bupivacaine Depression of Cardiac Conduction: Fast Block Sodium Channels during the Action Potential with Slow Recovery from Block during Diastole" Anesthesiology 62:396–405.

Courtney, K.R., J.J. Kendig (1988) "Bupivacaine is an effective potassium channel blockbuster in heart" Biochimica et Biophysica Acta 939:163–166.

Denson, D.D. et al. (1992) "Entiomer–Specific Effects of an Intravenously Administered Arrhythmogenic Dose of Bupivacaine on Neurons of the Nucleus Tractus Soliatrus and the Cardiovascular System in the Anesthetized Rat" Regional Anesthesia 17:311–316.

Vanhoutte, F. et al. (1991) "Stereoselective effects of the enantiomers if bupivacaine on the electrophysiological properties of the guinea–pig papillary muscle" Br. J. Pharmacol. 103:1275–1281.

Valenzuela, C. et al. (1994) "Stereoselective Bupivacaine Block of the Human Cardiac Delayed Rectifier Kv1.5 Channel" Biophys. J. 66:A205, abstract No. Tu–Pos383.

Aps, C., F. Reynolds (1978) "An Intradermal Study of the Local Anaesthtic and Vascular Effects of the Isomers of Bupivacaine" Br. J. Clin. Pharmac. 6:63–68.

Burm, A.G.L. (1994) "Pharmakinetics of the enantiomers of bupivacaine following intravenous administration of the racemate" Br. J. Clin. Pharmac. 38:125–129.

Reynolds, F. (1995) "In defence of bupivacaine" International Journal of Obstetric Anesthesia 4:93–108.

* cited by examiner

LEVOBUPIVACAINE AS AN ANALGESIC AGENT

CROSS-REFERENCE TO RELATED APPLICATIONS

This application is a continuation of U.S. patent application Ser. No. 09/210,966, filed Dec. 14, 1998 now U.S. Pat. No. 6,103,741, which is a continuation of Ser. No. 08/549,408, filed Oct. 27, 1995, now U.S. Pat. No. 5,849,763; which is a continuation-in-part of PCT/GB94/02249, filed Oct. 13, 1994.

FIELD OF THE INVENTION

This invention relates to a new therapeutic use for levobupivacaine or (S)-1-butyl-N-(2,6-dimethylphenyl)-2-piperidinecarboxamide.

BACKGROUND OF THE INVENTION

Racemic bupivacaine is an effective long-acting local anesthetic, and may be given as an epidural. However, racemic bupivacaine is cardiotoxic, having depressant electrophysiological and mechanical effects on the heart. It should therefore be used with caution in cardiac-compromised patients, and the use of high doses and high concentrations is contraindicated.

In particular, bupivacaine has produced death in a number of patients, including women in childbirth and when used in the Bier's block technique. Although the incidence of death has been relatively small, the concern has been sufficient to stop the use of 0.75% bupivacaine for obstetrics and the prescribing of bupivacaine for use in Bier's blocks.

In addition, due to its mode of action, directly on the nervous system, at higher doses bupivacaine is known to have undesirable central nervous system (CNS) side-effects which, prima facie, are connected to its anesthetic activity. Indeed, the occurrence of CNS side-effects is one of the major factors limiting the use of this drug in normal clinical practice employing techniques such as local infiltration, nerve block, field block, epidural and spinal blocks.

It is known that levobupivacaine is probably less cardiotoxic than dexbupivacaine and racemic bupivacaine. See, for example, Vanhoutte et al. (1991) *Br. J. Pharmacol.* 103:1275–1281, and Denson et al. (1992) *Regional Anaesthesia* 17:311–316. Vanhoutte et al. studied the effects of bupivacaine enantiomers on the electrophysiological properties of guinea pig isolated papillary muscle; this is based on their statement that "the cardiotoxicity of bupivacaine seems to be mainly of electrophysiological origin."

BRIEF SUMMARY OF THE INVENTION

Surprisingly, it has now been found that while levobupivacaine retains the anesthetic activity of the racemate, it produces less CNS side-effects, i.e., the CNS side-effects and the anesthetic activity of levobupivacaine are not inter-related in the same manner as in racemic bupivacaine. Expressed in another way, the therapeutic ratio of levobupivacaine with respect to CNS side-effects is unexpectedly higher than it is for the racemic drug. This, coupled with the known reduced cardiac side-effects of levobupivacaine, means that levobupivacaine is useful as a local anesthetic, particularly in clinical procedures where the risk of systemic exposure to the drug is increased, and harmful side-effects are associated therewith. Indeed, it may be useful in any clinical procedure in which the racemic drug has, or may have, a debilitating effect. In addition, while levobupivacaine can be used at doses conventionally used for the racemic drug, it can also be used at higher doses and/or over longer periods, formerly contraindicated for the racemic drug, enabling better anesthesia, e.g., in terms of availability to different patient types, extent of anesthetic block achieved, etc., without the adverse effects conventionally associated with these dose regimens.

According to a first aspect of the present invention, a method of providing anesthesia, in particular without concomitant adverse systemic side-effects (e.g., CNS), in a patient, comprises administering to the patient an effective amount of levobupivacaine.

According to a second aspect of the present invention, a method of providing anesthesia in obstetrics comprises administering to a patient levobupivacaine.

According to a third aspect of the present invention, a pharmaceutical composition comprises a solution, preferably aqueous, having a concentration of greater than 0.75% w/v of levobupivacaine, measured as the free base.

According to a fourth aspect of the present invention, a unit dose of levobupivacaine comprises an ampoule containing the above-described composition.

DETAILED DISCLOSURE OF THE INVENTION

For the purpose of the present invention, CNS side-effects include effects such as tinnitus, numb tongue or lips, and dry mouth, and are the early indicators of direct nervous system effects. For instance, CNS side-effects are typically used as warnings of the onset of convulsions (which in a pregnant woman may also be induced in utero) which must be avoided because of the risk to the patient, e.g. death, brain damage, foetal distress, etc. As a result, clinical administration of a local anesthetic is stopped upon onset of these early symptoms, whether or not adequate anesthesia or analgesia has been achieved. The dose at which CNS side-effects appear varies greatly between patients and cannot be predicted reliably.

In the method of the present invention, levobupivacaine may be provided in solution, for infusion or injection into the epidural or spinal space, or for administration by any of the conventional means for obtaining a nerve or field block. In addition to the anesthetic blocks conventionally provided by the racemate, levobupivacaine may also be useful in providing blocks in areas of the body where the risk of systemic exposure to the drug, and therefore CNS side-effects, is particularly high. Examples include open wounds and vascular areas, for instance using intercostal blocks for the latter.

Administration of levobupivacaine may be continuous or bolus administration. This may be done using conventional apparatus, e.g., including means for the patient to induce infusion as desired. The daily dose administered to the patient may be in the relatively low range known for the administration of racemic bupivacaine but, because of the decreased CNS side-effects of levobupivacaine, may be higher than the conventional dose for the racemic drug. For instance, the patient may receive a daily dose of levobupivacaine of up to about 2500 mg. However, it is preferred to provide a considerable safety margin for the patient and, therefore, for the patient to receive a daily dose of less than about 2000 mg. Consequently, the total dose of levobupivacaine may be around, or in excess of, about 2 mg per kg of patient body weight.

The concentration of levobupivacaine to be given can be that conventionally used for the racemic drug. However, the concentration is typically higher than this, for instance, at least about 0.75% w/v, and can be up to about 2% w/v. Preferably, however, the concentration of levobupivacaine is in the range of about 0.8% to about 1.5% w/v, and more preferably a concentration of about 1%, 1.25%, or 1.5% w/v is used. The solution is preferably aqueous.

The solution may typically be put up in unit doses of from about 1 to about 15 ml, and preferably of about 10 ml. However, the unit doses may be higher, for example, up to about 40 ml or higher. The unit doses my be in the form of ampoules, which may be made of any suitable material, e.g., glass or an appropriately impervious plastic material. Unit dosages comprising at least about 75 mg, but preferably less than about 200 mg, of levobupivacaine can be administered, and more preferably the unit dosage is in the range of about 80 to about 150 mg. Consequently, the patient may receive a daily dose of levobupivacaine of up to about 2500 mg, but it is preferred that the daily dose is less than about 2000 mg.

The administration of levobupivacaine over a range of concentrations, including those currently used for the racemic drug and the higher concentrations described above, can be carried out for significantly longer periods than at present, again as a result of the reduced CNS side-effects experienced with levobupivacaine. For example, levobupivacaine can be administered to a patient safely for at least 24 hours, often up to 72 hours, and even for periods of up to a week or a fortnight, or longer. It can, of course, be administered for similar periods already used for the racemic drug, e.g., between about 3 and 6 hours.

The method of the present invention is particularly useful in surgical procedures carried out on patients who are cardiac- or CNS-compromised, or patients predisposed to cardiac- or CNS-related conditions, i.e., having a low CNS threshold. Alternatively, the patient may be one in which the direct nervous system effects following CNS side-effects are particularly dangerous, or even lethal, e.g, a pregnant woman, and especially a woman in, or about to start, labour or to undergo Caesarian section.

The levobupivacaine used in the present invention is preferably substantially free of dexbupivacaine, and is more preferably in at least 90%, and most preferably at least 99%, enantiomeric excess with respect to dexbupivacaine. Throughout this specification, reference to bupivacaine and its enantiomers includes pharmaceutically-acceptable salts thereof.

Following are examples which illustrate procedures for practicing the invention. These examples should not be construed as limiting. All percentages are by weight and all solvent mixture proportions are by volume unless otherwise noted.

EXAMPLE 1

Physiological Effects of Levobupivacaine Administration

The cardiovascular and central nervous (CNS) effects of levobupivacaine were compared with racemate (Marcaine) in healthy male volunteers. Drugs were administered by intravenous administration in a double-blind crossover manner. The infusion rate was 10 mg/minute for each drug, and infusion was continued up to a maximum of 150 mg or stopped following the first detection of CNS effects (including tinnitus, numb tongue or lips, and dry mouth). Volunteers were previously conditioned to the CNS effects of local anesthetics by administration of a test dose of lignocaine. A range of cardiovascular parameters were measured, including systolic and diastolic blood pressures, ECG, and, using the transthoracic electrical bioimpedance technique (with a BoMed NCCOM3-R7), aortic blood flow, allowing measurements of cardiac index and stroke index. Based on results from a previous study in which racemic bupivacaine was infused, it was anticipated that the major cardiovascular changes observed following bupivacaine administration would be related to myocardial contractility. Therefore, an acceleration index, representing the initial maximum acceleration of blood flow during the onset of ejection, was measured to estimate myocardial contractility in this new study.

Levobupivacaine, like racemate, was well tolerated. The mean total doses administered of levobupivacaine and racemate, before the onset of CNS effects, were 54.0 and 45.6 mg, respectively, and plasma concentrations at the end of infusion were 2.384 $\mu$g/ml and 1.87 $\mu$g/ml, respectively (n=12). Despite the mean total dose and plasma concentration being higher with levobupivacaine, this produced much smaller mean changes in cardiac variables than the racemate. The myocardial contractility index was significantly reduced by bupivacaine from a value of 1.36 $S^{-2}$ to 1.18 $S^{-2}$, a decrease of 0.18 $S^{-2}$ or 13%.

For levobupivacaine, the pre-dose value was 1.34 $S^{-2}$, and this only decreased to 1.28 $S^{-2}$ at the end of infusion, a decrease of 0.06 $S^{-2}$ or 4.5%. The difference between drug treatments was highly significant ($p<0.02$, n=12). The results were similar for stroke index, a parameter likely to reflect changes in myocardial contractility. Bupivacaine reduced this from 55.3 ml/$M^2$ to 44.4 ml/$M^2$, a decrease of 10.9 ml/$M^2$ or 20%. For levobupivacaine, the pre-dose value was 52.4 ml/$M^2$ and 49.1 ml/$M^2$ at the end of infusion, a decrease of 3.3 ml/$M^2$ or 6%. Again, the difference between drug treatments was statistically highly significant ($p<0.01$, n=12). Small changes in other variables occurred including heart rate and mean blood pressure (increases) and ejection fraction and cardiac index (decreases). As with acceleration index and stroke index, the changes tended to be greater with bupivacaine.

As is apparent from the above, a larger quantity of levobupivacaine was required to stimulate CNS effects than racemic bupivacaine: in the 12 volunteers, the mean total dose of levobupivacaine administered was 54.0 mg compared with 45.6 mg of racemic bupivacaine.

EXAMPLE 2

Composition of an Aqueous Solution of Levobupivacaine

A sterile isotonic solution of levobupivacaine was made up using the following components:

1.00 g of levobupivacaine hydrochloride (measured as the free base)

0.9 g of sodium chloride to 100 ml water for injection

The solution was made up under sterile conditions (alternatively, it could have been sterilized after make-up, e.g., by sterile filtration).

10 ml aliquots of the solution were filled into sterilized glass ampoules, which were then sealed ready for use.

It should be understood that the examples and embodiments described herein are for illustrative purposes only and that various. modifications or changes in light thereof will be suggested to persons skilled in the art and are to be included within the spirit and purview of this application and the scope of the appended claims.

What is claimed is:

1. A unit dose of levobupivacaine wherein said unit dose provides anesthetic activity in a patient without adverse CNS side effects comprising at least 75 mg to less than 200 mg of levobupivacaine.

* * * * *